(12) United States Patent
Glaser et al.

(10) Patent No.: US 11,690,655 B2
(45) Date of Patent: Jul. 4, 2023

(54) MONOLITHIC PERCUTANEOUS-SCREW SYSTEM FOR SPINAL SURGERIES

(71) Applicant: Warsaw Orthopedic, Inc., Warsaw, IN (US)

(72) Inventors: Adam Glaser, Germantown, TN (US); R. Quinn Brown, Collierville, TN (US); Daniel Wall, Cordova, TN (US); Joshua Simpson, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 279 days.

(21) Appl. No.: 16/746,222

(22) Filed: Jan. 17, 2020

(65) Prior Publication Data

US 2021/0220022 A1 Jul. 22, 2021

(51) Int. Cl.
*A61B 17/70* (2006.01)
*A61B 17/90* (2006.01)

(52) U.S. Cl.
CPC ...... *A61B 17/7076* (2013.01); *A61B 17/7001* (2013.01); *A61B 17/90* (2021.08)

(58) Field of Classification Search
CPC ........ A61B 17/70; A61B 17/7074–708; A61B 17/7083–7085
See application file for complete search history.

(56) References Cited

U.S. PATENT DOCUMENTS

| | | | |
|---|---|---|---|
| 10,383,675 B1 | 8/2019 | Cummins et al. | |
| 2010/0174325 A1* | 7/2010 | Won | A61B 17/7037 606/305 |
| 2011/0202095 A1* | 8/2011 | Semler | A61B 17/8605 606/305 |
| 2016/0008034 A1* | 1/2016 | Stokes | A61B 17/708 606/278 |
| 2016/0296266 A1 | 10/2016 | Chandanson et al. | |
| 2018/0243022 A1 | 8/2018 | Marek et al. | |
| 2019/0290332 A1* | 9/2019 | Tsuang | A61B 17/8605 |
| 2019/0307493 A1* | 10/2019 | Jackson | A61B 17/7091 |
| 2019/0343558 A1* | 11/2019 | Farmer | A61B 17/7085 |

FOREIGN PATENT DOCUMENTS

WO 2004032726 A2 4/2004

OTHER PUBLICATIONS

European Patent Office, 80298 Munich Germany, European Search Report, Application No. 151315.5-1 132, Applicant: Warsaw Orthopedic, Inc., dated Jun. 16, 2021.

* cited by examiner

*Primary Examiner* — Eduardo C Robert
*Assistant Examiner* — Michelle C Eckman
(74) *Attorney, Agent, or Firm* — Sorell, Lenna & Schmidt, LLP

(57) ABSTRACT

In one aspect, the present disclosure provides a monolithic percutaneous-screw system for use in spinal surgery. The system includes (i) a receiver having a distal base and a pair of opposing arms extending proximally from the base, a pair of opposing distal breakoff sections, each connected monolithically to a proximal end of a corresponding one of the arms, (ii) a pair of opposing proximal breakoff sections, (iii) a pair of opposing intermediate extenders, each extending from a distal end, connected monolithically to a corresponding one of the distal breakoff sections, to a proximal end connected monolithically to a corresponding one of the proximal breakoff section, and (iv) a guide cap connected monolithically to both of the proximal breakoff sections.

20 Claims, 11 Drawing Sheets

MONOLITHIC PERCUTANEOUS-SCREW SYSTEM FOR SPINAL SURGERIES

FIELD

The present disclosure relates to systems for spinal surgery, generally, and, more particularly to monolithic percutaneous-screw systems for spinal surgeries.

BACKGROUND

Spinal pathologies and disorders such as scoliosis, kyphosis, and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders.

Surgical treatment of these spinal disorders includes correction, fusion, fixation, discectomy, laminectomy and implantable prosthetics.

Surgical rods are used commonly in correcting spinal abnormalities. Pedicle-screw assemblies are often used to facilitate securement of one or more spinal rods relative to the spine. Pedicle-screw assemblies include a bonescrew attached to a rod-receiving receiver. The bonescrews are attached to patient vertebrae, and the receivers receive portions of the spinal rod.

The receivers of typical pedicle-screw assemblies are in some cases angularly positionable with respect to the bonescrew to facilitate select orientation of the spinal rod with respect to the vertebrae. With the bonescrews fixed to the vertebrae, a user can in connecting the rod to the receiver persuade the spine toward a desired shape.

Percutaneous pedicle fixation is a minimally invasive surgical technique involving placing pedicle screws and spinal rods through very small skin incisions. Surgeons in some cases attach external extender instruments to heads of the pedicle screws. The extender instruments can facilitate rod reduction, or maneuvering the rod into place in the heads. There is need for spinal implant systems that enable robust rod reduction without external extender instruments.

SUMMARY

Systems and processes of the present disclosure relate generally to monolithic percutaneous-screw systems for use in spinal surgeries, such as minimally invasive spinal surgeries.

In one aspect, the present disclosure provides a monolithic percutaneous-screw system for use in spinal surgery. The system includes (i) a receiver having a distal base and a pair of opposing arms extending proximally from the base, a pair of opposing distal breakoff sections, each connected monolithically to a proximal end of a corresponding one of the arms, (ii) a pair of opposing proximal breakoff sections, (iii) a pair of opposing intermediate extenders, each extending from a distal end, connected monolithically to a corresponding one of the distal breakoff sections, to a proximal end connected monolithically to a corresponding one of the proximal breakoff section, and (iv) a guide cap connected monolithically to both of the proximal breakoff sections. The proximal breakoff sections are each sized and shaped such that the proximal breakoff section can be readily broken by a user when a first moment, along a first plane, is applied to the cap. And the distal breakoff sections are each sized and shaped such that the distal breakoff section (a) is not broken when a user applies the first moment to the cap, and (b) can be readily broken by the user when a second moment, along a second plane, generally orthogonal to the first plane, is applied to the extender.

In another aspect, the disclosure provides a monolithic percutaneous-screw system for use in spinal surgery. The system includes the four components referenced above ((i)-(iv)). An outer lateral surface of each distal breakoff section is setback from an adjacent outer surface of a corresponding one of the receiver arms connected to the distal breakoff section. Each of two end surfaces of each distal breakoff section is setback from an adjacent side surface of a corresponding one of the receiver arms connected to the distal breakoff section. An outer lateral surface of each proximal breakoff section is setback from an adjacent outer surface of a corresponding one of the extenders connected to the proximal breakoff section. And each of two end surfaces of each proximal breakoff section is setback from an adjacent side surface of a corresponding one of the extenders connected to the proximal breakoff section.

In yet another aspect, the disclosure provides a monolithic percutaneous-screw system for use in spinal surgery. The system includes the four components referenced above ((i)-(iv)). Various optional features are described. The proximal breakoff sections are each sized and shaped such that the proximal breakoff section can be readily broken by a user when a first moment, along a first plane, is applied to the cap, for instance.

The distal breakoff sections are each sized and shaped such that the distal breakoff section (i) is not broken when a user applies the first moment to the cap, and (ii) can be readily broken by the user when a second moment, along a second plane, generally orthogonal to the first plane, is applied to the extender.

The size of the proximal breakoff section includes the proximal breakoff section having a short length, measured between ends of the proximal breakoff section, as compared to a length of the distal breakoff section, measured between ends of the distal breakoff section.

The proximal breakoff sections are each sized and shaped such that the proximal breakoff section can be readily broken by a user when a first moment, along a first plane, is applied to the cap. The distal breakoff sections are each sized and shaped such that the distal breakoff section (i) is not broken when a user applies the first moment to the cap, and (ii) can be readily broken by the user when a second moment, along a second plane, generally orthogonal to the first plane, is applied to the extender. And the shape of the distal breakoff section includes lateral surfaces of the distal breakoff section being concave.

In various embodiments, an outer lateral surface of each distal breakoff section is setback from an adjacent outer surface of a corresponding one of the receiver arms connected to the distal breakoff section.

In various embodiments, an outer lateral surface of each distal breakoff section is setback from an adjacent outer surface of the corresponding extender connected to the distal breakoff section.

In various embodiments, each of two end surfaces of each distal breakoff section is setback from an adjacent side surface of a corresponding one of the receiver arms connected to the distal breakoff section. Each of two end surfaces of each distal breakoff section may be setback from an adjacent side surface of a corresponding one of the extenders connected to the distal breakoff section.

In various embodiments, an outer lateral surface of each proximal breakoff section is setback from an adjacent outer surface of a corresponding one of the extenders connected to the proximal breakoff section.

In various embodiments, an outer lateral surface of each proximal breakoff section is setback from an adjacent outer surface of the cap connected to the proximal breakoff section.

In various embodiments, each of two end surfaces of each proximal breakoff section is setback from an adjacent side surface of a corresponding one of the extenders connected to the proximal breakoff section.

In various embodiments, each of two end surfaces of each proximal breakoff section is setback from an adjacent outer surface of the cap connected to the proximal breakoff section.

In various embodiments, each intermediate extender has an inner wall and an outer wall, the inner walls having an extender threadform, each arm has an inner wall and an outer wall, the inner walls having a receiver threadform, and the extender threadforms are sized, shaped, and clocked to match the receiver threadform such that a setscrew can thread smoothly through the extender threadforms proximally onto the receiver threadform. In some cases, each threadform has a helical flange format for receiving a helical-flange setscrew, the threadform defining a thread channel having a proximally extending space for receiving a proximally extending flange of a setscrew thread.

In various embodiments, the cap has a proximal end having a generally circular cross section. In some case, the proximal end of the cap has a radially inner transition portion having a curved or beveled surface to facilitate guiding external media into a central channel of the cap in operation of the system. In some case, the cap has opposing arched distal cutouts.

In various embodiments, the cap has opposing arched distal cutouts, and each extender includes opposing transition surfaces sloping from a proximal end of the extender to a corresponding side wall of the extender, each sloping surface opposing one of the arched distal cutouts.

In various embodiments, each extender transition surface extends with respect to an adjacent side wall of the extender by an angle of between about 30 degrees and about 60 degrees, and each distal cutout extends with respect to an adjacent exterior wall of the cap by an angle of between about 30 degrees and about 60 degrees.

Details of various aspects of the disclosure are set forth in the accompanying drawings and description below. Other features, objects, and advantages of the technology will be apparent from the description, drawings, and claims.

DETAILED DESCRIPTION

The present technology includes monolithic percutaneous-screw systems. The systems can be used in minimally invasive spinal surgeries, such as in the thoracic, thoracic-lumbar or lumbar regions.

Example surgeries include but are not limited to spinal surgeries for correcting or improving patients with adolescent idiopathic scoliosis, or AIS surgery.

Benefits of the present technology include obviating need for external extenders, saving manufacturing/product cost, storage space, shipping needs, and time and work in the procedure. Time is saved by none being needed to connect external extenders to a rod receiver, or any cap, for instance. There is also no chance to mis-assemble external extenders to the rod receiver or any cap.

extender instruments by a perc screw head having an extended the rod-slot height. Functionality of the systems is also benefited by geometries facilitating ease and safety in separation of select portions of the system after implantation and building of a rodded spinal-correction construct.

Figure 1:
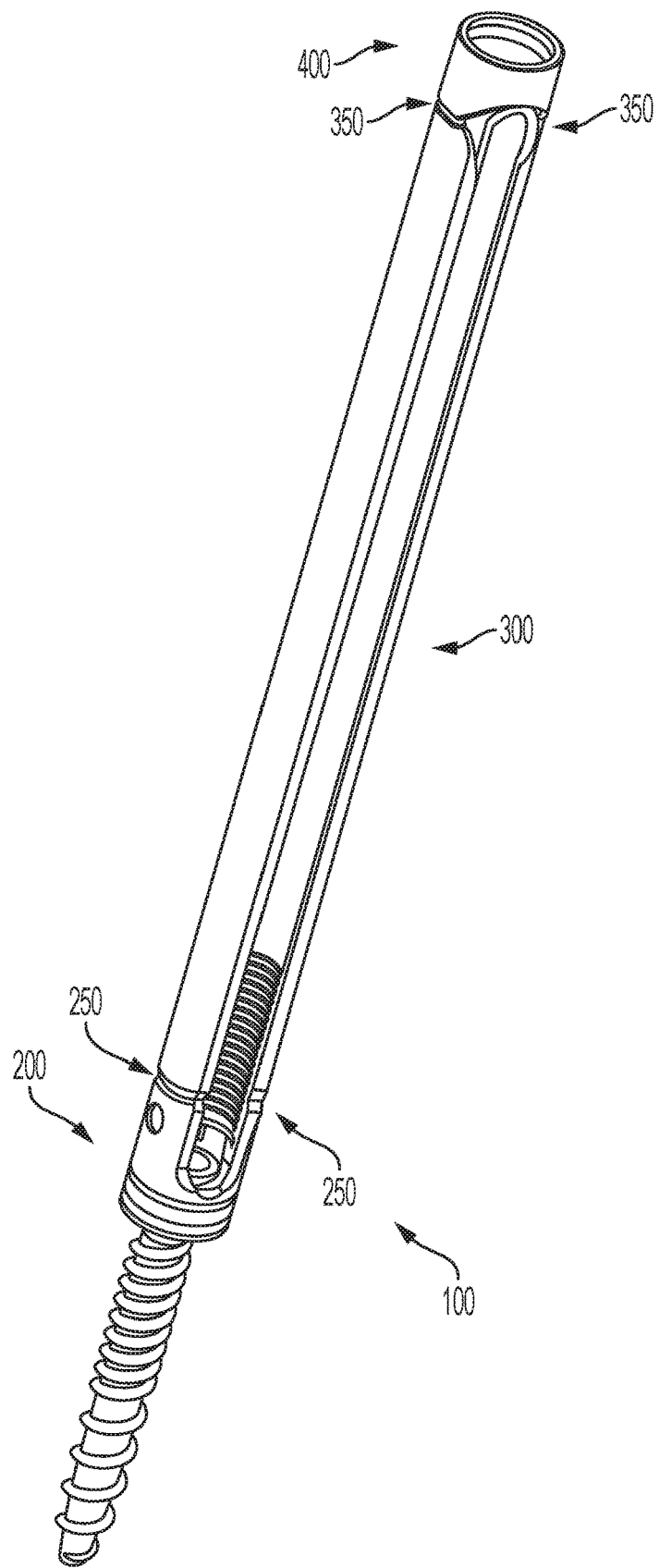
FIG. 1 is a perspective view of a monolithic percutaneous pedicle screw system according to embodiments of the present technology.

Turning now to the drawings, and more particularly to the first figure, FIG. 1 is a perspective view of a monolithic percutaneous pedicle screw system. The system is referenced by numeral 100 in the drawings.

The system 100 includes a distal receiver assembly 200 connected by an intermediate intrinsic extender component 300 to a proximal guide cap 400. The term intrinsic is used in connection with the nature of the extender 300 being connected monolithically, or unitarily, with the adjacent cap 400 and receiver 220.

The breakoff section 300 is connected to the receiver assembly 200 by a first, distal, breakoff section 250. And to the guided cap 400 by a second, proximal, breakoff section 350.

These components, sections, and a multiple-cap removing-and-holding instrument, are described further in turn with reference to FIGS. 2-13.

Figure 2:
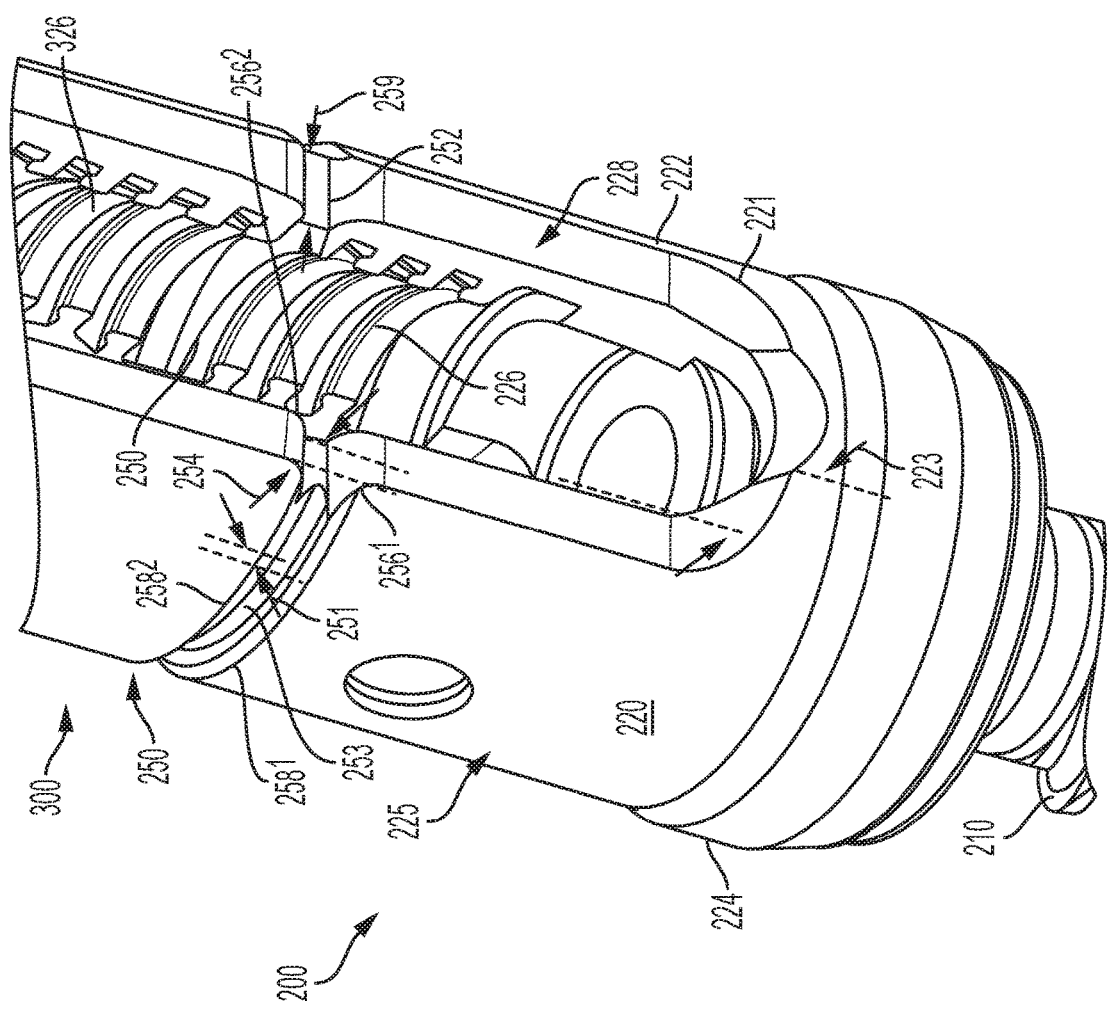
FIG. 2 is a perspective view of a proximal portion of a receiver assembly connected by a first, distal, breakoff section to a distal portion of an intrinsic extender of the system of FIG. 1.

FIG. 2 is a perspective view of a proximal portion of the receiver assembly 200 and a distal portion of the intrinsic extender 300 of the system 100 of FIG. 1. The receiver assembly includes or is attached to a bonescrew 210, and a receiver 220 connected to the bonescrew 210. A head of the bonescrew 210 and head-receiving components of the receiver 220 are in various embodiments configured such that the head can be readily pushed into, or popped in, to the receiver 220 and the head-receiving components would hold the head and so the bonescrew in place against the receiver 220. In use of the system 100, the bonescrew 210 is anchored to a patient vertebra—to a pedical region thereof, for instance. The system 100 may in these cases include the term pedical, such as monolithic percutaneous pedical screw system.

The receiver assembly 200 can be configured in a uni-axial format such that the receiver 220 can be moved only along a single plane with respect to the bonescrew 210, or a multi-axial format such that the receiver 220 can be moved anywhere within a generally conical space with respect to the bonescrew 210. The receiver 220 and bonescrew 210 has, in a contemplated embodiment, a fixed format, whereby the receiver 220 does not more with respect to the screw 210.

For multi- and uni-axial formats, a head of the bonescrew 210 extends into a distal cavity (not shown in detail) of the receiver 220, and the head is movable within the cavity.

The receiver 220 includes opposing receiver arms 222 extending from a receiver base 224. The arms 222 define a rod slot between them.

Each receiver arm 222 extends from a distal end to a proximal end, between side edges or walls 228, and between an outer wall and an inner wall having a threadform 226. The threadform is in various embodiments has a helical-flange format, as described further in connection with FIG. 13.

The sidewalls 228 of the receiver arms 222 are in some embodiments recessed, setback, or offset, by a distance 223, from an outer diameter (whether a maximum OD) of the receiver base 224. Having the arms 222 extend radially out less than the base 224 gives the receiver 220 and so the system 100 a relatively lower profile, enabling improved visibility around the receiver 100, and lowering material cost and weight without compromising strength.

The setback arms 222 are connected to the base 224 by a curved transition 221. The gradual change promotes strength in the transition 221. And the gradual interface limits effects of edging, such as by lowering chances of a surgeon or assistant accidentally ripping a sterile glove in handling the receiver 220. The slight transition 221 also makes the area gentler on any adjacent patient tissue.

The first, distal, breakoff section 250 connects the receiver 200 to the intrinsic extender 300 monolithically. The section 250 is connected to the receiver 200 and the extender 300 in a unitary manner, for instance, verses being snapped, snug, fit, or otherwise connected to each other by an end user. The connection can include the receiver, breakoff section, and extender being formed together, or semi-permanently attached (such as by welding), in original manufacturing of the system 100, for example.

The breakoff section 250 can be configured in any of a variety of ways to be weaker for breaking. In some embodiments, the breakoff section 250 is weaker by (A) being thinner than a thickness (measured from inner wall to outer wall) of one or both of (i) arms 222 of the receiver 220 and (ii) the intrinsic extender 300, and/or (B) having a width (from end to end of the section 250) that is less than a width of the adjacent (i) arms 222 of the receiver 220 and/or (ii) the intrinsic extender 300. The section 250 can instead or also be configured for ready breaking based on its material, such as by including a material that is frangible or relatively brittle, relative to adjacent material of the arms 222 and/or extender 300.

Portions of the breakoff section 250 are in various embodiments offset, recessed, or setback, in one or more portions. End walls 252 of the section 250 can be setback by a distance 254 from adjacent sidewalls 228 of the receiver 220, for instance. Less material at the breakoff section can have benefits including lower material cost and weight, without compromising strength of the section 250. Offsetting of the distal breakoff section 250 can also include an outer lateral surface 253 of the section 250 being spaced by a predetermined distance 251 from the adjacent outer wall 225 of the receiver 220. Benefits of the offsetting also lowers effects of edging, such as by lowering chances of the surgeon or assistant accidentally ripping or catching a sterile glove in handling the receiver 220 after the intrinsic extender 300 has been broken from the receiver 220 (reference FIG. 6). The broken breakoff section 250 may have some roughness, for instance, that can be better avoided with the section being setback from adjacent material in this way. The offsetting also makes the area gentler on any adjacent patient tissue after the break, as compared to the broken section 250 extending further or fully to adjacent surface(s) 225 of the arm 222, such as to the top of the arm wall 228 and to the outer wall of the receiver 220.

The receiver 220 can also have low-profile transition portions, for lowering weight, material cost, effect on adjacent tissue post-surgery, and especially the chance of ripping or catching a sterile surgical glove. Example transition portions include curved or beveled proximal side edges 258[1] of the receiver 220, and curved or beveled distal side edges 258[2] of the intrinsic receiver 300. The low-profile transition portions can also include beveled or curved side ends 256[1] of the receiver 220, and curved or beveled distal side ends 256[2] of the intrinsic receiver 300. Benefits of such receiver-extender include benefits analogous to any of the those provided above in connection with the breakoff-section offsetting.

The receiver 220 inner threadform 226 has a configuration corresponding to an inner threadform 326 of the intrinsic extender 300. The configuration includes sizing, shape, orientation, and positioning. The two threadforms 226, 326 are clocked to match each other, for instance, so that a setscrew 1350 (FIG. 13) can be readily and smoothly threaded from the extender threads to the receiver threads 226 for locking down the spinal rod (not shown) in the rod slot defined by the receiver arms 222.

In various embodiments, a height of the extender threadform, measured in a longitudinal, distal-to-proximal, direction, is greater than a height of the receiver threadforms. The extender-threadform height is in some cases greater than twice the receiver-threadform height.

Figure 3:
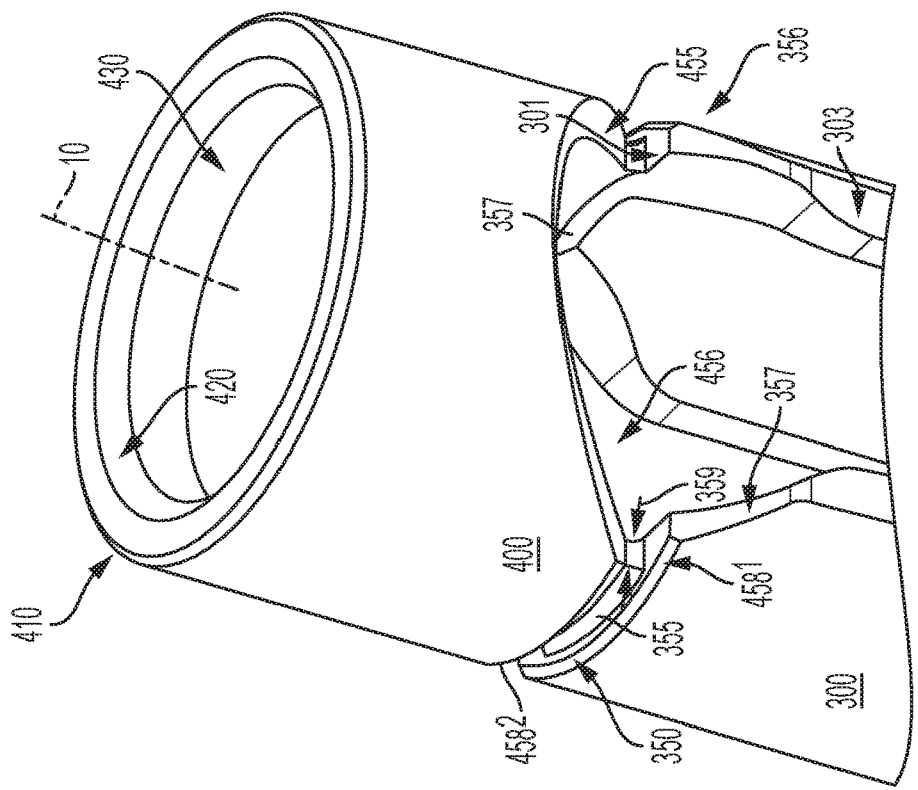
FIG. 3 is a perspective view of a guide cap connected by a second, proximal, breakoff section to a proximal portion of the intrinsic extender of the system of FIG. 1.

FIG. 3 is a perspective view of the guide cap 400. The cap 400 is in various embodiments generally cylindrical, and round in profile. Benefits of the cap being rounded can include the cap having no drastic edging at the proximal end, as compared to the higher edging formed by the proximal ends 301 of the extenders 400, which extend radially away from a centerline of the extender proximal end until a points at which the end surface terminates and the surface transitions (reference transition area 356 in FIG. 3, for instance), to extender side walls 303. The rounded proximal end of the cap 400 thereby lowers the chance of other objects, such as a surgeon's glove, implant or instrument catching on the cap 400. The round or circular shape of the cap 400, or at least proximal end thereof, also benefits the guiding function of the cap, better guiding instruments into and through the cap 400 and downstream channeling of the instrument along the longitudinal axis 10.

The guide cap 400 is connected monolithically by the second, proximal, breakoff section 350 to a proximal portion of the intrinsic extender 300 of the system 100 of FIG. 1. The section 350 is connected to the cap 400 and the extender 300 in a unitary manner, for instance, verses being snapped, snug fit, or otherwise connected to each other by an end user. The connection can include the cap, breakoff section, and extender being formed together, or semi-permanently attached (such as by welding), in original manufacturing of the system 100, for example.

The proximal breakoff section 350 can be configured in any of a variety of ways to be weaker for breaking. In some embodiments, the proximal breakoff section 350 is weaker by (A) having a thickness 359 that is thinner than a thickness (measured from inner wall to outer wall) of one or both of (i) adjacent walling of the guided cap 400 and (ii) adjacent walling of the intrinsic extender 300, or (B) having a width (from end to end of the section 350) that is less than a width of the adjacent (i) guide cap 300 and/or (ii) the intrinsic extender 300. The section 350 can instead or also be configured for ready breaking based on its material, such as by including a material that is frangible or relatively brittle (relative to adjacent material of the guide cap 400 and/or extender 300).

The second breakoff section 350 can be offset, recessed, or setback from lateral and side edges or walls of the intrinsic extender 300, in ways, and for analogous reasons, that the first breakoff section 250 can be setback in one or more portions, as described above in connection with FIG. 2.

In various embodiments, the second breakoff section 350 is configured to breakoff by application of a moment or force in a different manner than moment or force that snaps the first breakoff section 250. While the maneuver can involve application of a moment, force, or combination, the action is referred to for simplicity here as a moment, considered to include these unless explicitly described or claimed otherwise herein.

In some embodiments, the moment required to snap the first and second breakoff sections 250, 350 can be in opposite directions—e.g., along orthogonal or perpendicular planes. In one case, the second breakoff section 350 is configured to be broken along a sagittal plane, or in a sagittal direction, in the patient reference frame, and the first breakoff section 250 is configured to be broken off by medial-to-lateral moment, or in a medial-lateral direction.

Figure 4:
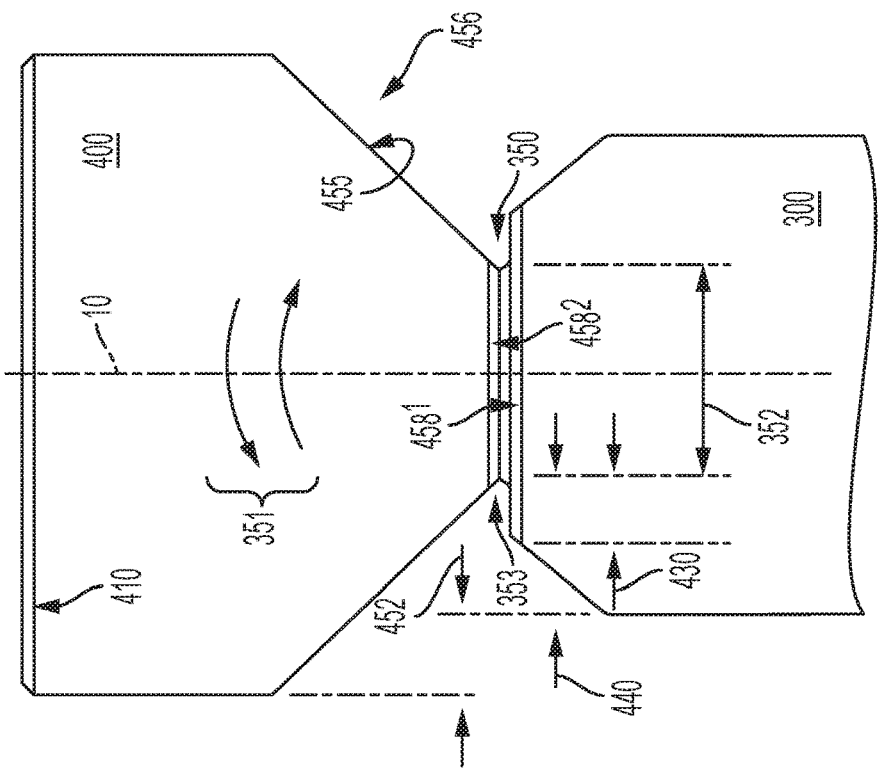
FIG. 4 is a side view of the parts shown in FIG. 3.

Regarding the example breaking direction of the proximal breakoff section 350, which is in various implementations snapped before the distal breakoff section 250, reference is made to FIG. 4, in cases in which the system 100 is implanted such that the plane of the page having FIG. 4 would be along the patient's sagittal plane, then sagittal-directed moment would rock the top or proximal end of the cap 400 towards the left, or toward the right, along a curve. The sagittal motion is indicated generally by arrows 351 in the view.

Figure 9:
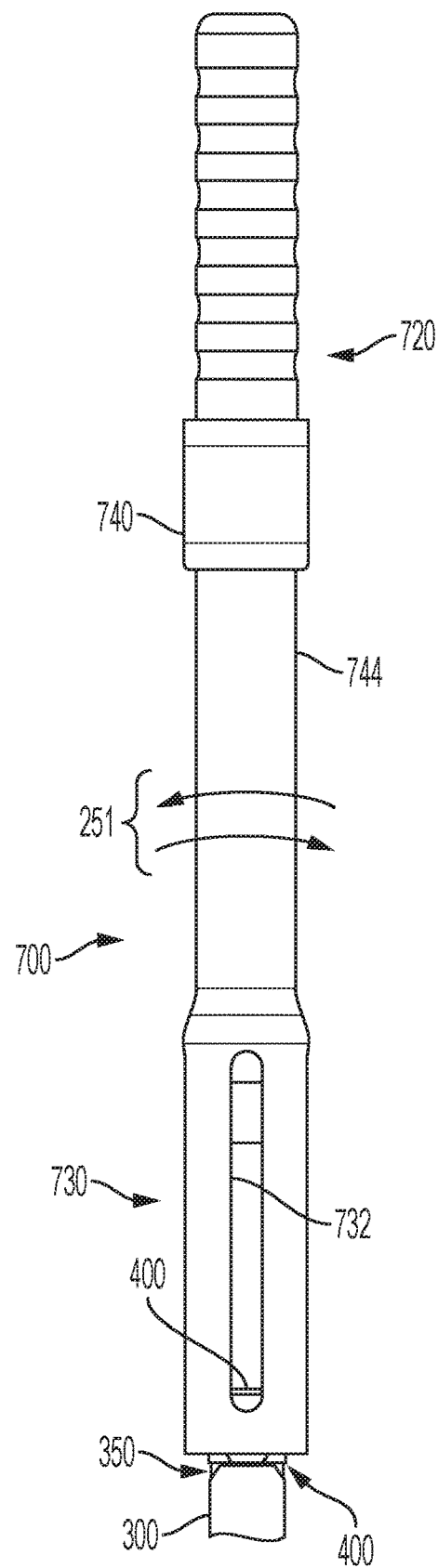
FIG. 9 is a closer view of the remover instrument retrieving the guide cap.

Regarding the example breaking direction of the distal breakoff section 350, which is in various implementations snapped after the proximal breakoff section 250, reference is made to FIG. 9. In cases in which the system 100 is implanted such that the plane of the page having FIG. 9 would be medial-lateral in the patient reference frame (i.e., the view looking at FIG. 9 would be looking sagittally, such as cranially or caudally (up or down the patient's spine), then application of a medial-lateral (or center, out) moment to the extender 300 would rock the proximal end of the extender 300 towards the left, or toward the right, along a curve. The medial-lateral motion is indicated generally by arrows 251 in the view.

Benefits of designing the system 100 so that the sections 250, 350 break most easily in response to moments in different directions, respectively, include better allowing a user to selectively break the system 100 at one of the sections without in that same motion breaking the system at the other section. The system 100 is in these embodiments designed for instance so that when a user applies a moment to the cap 400 along the sagittal plane, such as using the cap-removing tool 700, to readily snap the proximal breakoff section 350, the distal breakoff section 250 does not snap as well in the motion, the distal section 250 being designed to be stronger against sagittal-plane moment versus medial-lateral moment. The user can subsequently apply medial-lateral moment to the intrinsic extender 300, such as by an extender- or tab-breaking instrument (not shown), to snap the extender 300 at the distal section 250 from the receiver 220.

The system 100, including the breakoff sections 250, 350, can be configured in of various ways to promote the sections being more amenable to breaking in different respective directions. A primary example involves system 100 geometry, including size and shape. Various dimensions of the sections can be designed to promote breaking in response to predetermined moments. Width, length, and height are main examples. As an example, the relatively short length 352 of the proximal breakoff section 350 makes it easier to snap the cap 400 from the extender 300 at the section 350 by a moment applied to the cap along either direction 351 shown in FIG. 4, as compared to if the length 352 were longer. Regarding relative moment, or force, requirements for snapping between the two sections 250, 350, the proximal breakoff section 250 can have a greater length than the length 352 of the proximal section 350. A longer distal section 250 would resist snapping more in response to sagittal moment applied to the cap 400 and transmitted down to the section 250.

In contemplated embodiments, section surface shaping is configured to affect how the sections 250, 350 break, respectively. The proximal breakoff section 350 can have a curved (e.g., concave) end surface 353 (the short surface), making the section 350 easier to snap in response to moment along the directions 351 shown. In some embodiments, the surface 353 has at least one internal edge, or corner, such as by having a generally v-shape, versus having a fully curved concavity, and the concavity can be partially smooth leading generally radially inward to a generally v-shaped apex. Similarly, the distal breakoff section 250 can have a curved (e.g., concave) lateral surface 253 (the long surface), making the section 250 easier to snap in response to moment along the directions 251 (e.g., medial-lateral) shown in FIG. 9. A radially inner surface of the section 250, opposite the outer surface 253, can be curved for similar reasoning.

Along with breakoff-section material sizing and shaping being designed to make breaking easier in response to moments in select directions, sizing and shaping can be used to make breaking more difficult in response to moments in response to other directions. As an example, the end surface 252 of the distal breakoff section 250 is shown to be generally flat in FIG. 2, making it more difficult to snap the section 250 by moment applied to the system 100 along the sagittal plane (e.g., along the directions shown in FIG. 4). It is further contemplated that snap-resistance of the section 252 in response to moment in the sagittal plane can be increased by making the end surface 252 convex or being convex to some extent. Similar rationale can affect design of one or both lateral (radially inner and outer) surfaces 355, 357 (FIG. 3) of the proximal breakoff section 350. The surfaces 355, 357 can be designed to be flat or convex to some extent, for instance.

FIG. 4 is a side view of the parts shown in FIG. 3. Reference numeral 430 indicates a first example offset (e.g., sagittal-direction, or sagittal, offset), between a setback end surface 353 (measured from any point of the surface if not flat, such as at a radially inner most point) of the proximal breakoff section 350, and end or edge of the adjacent proximal end of the intrinsic extender 300.

FIGS. 3 and 4 also show the proximal end of the intrinsic extender 300 having a low-profile, or profile-lowering, transition portion 458[1], and the distal end of the guided cap 400 having a low-profile transition portion 458[2]. The proximal end of the intrinsic extender 300 can also include side low-profile transition portions 356, which can include a slope 357. The slope 357 can be curved or arched, and/or at either end of the slope be beveled or curved.

In various embodiments, each of the side transition portions 356—e.g., the slopes 357 thereof—extends at an angle with respect to an adjacent side wall 303 of the extender of between about 30 and 60 degrees, such as between about 40 and 50 degrees, such as approximately 45 degrees, all as shown in FIGS. 3 and 4.

The receiver 220 can also have low-profile transition portions, for lowering weight, material cost, effect on adjacent tissue post-surgery, and especially the chance of ripping or catching a sterile surgical glove. Example transition portions include curved or beveled proximal side edges 258[1] of the intrinsic receiver 300, and curved or beveled distal side edges 258[2] of the guide cap 400.

The guide cap 400 can further include a proximal external transition areas 410, such as a curved or beveled surface.

Benefits of the offsetting and transition portions lower effects of edges can include any of those described above regarding offsetting and transitioning between the receiver 220 and intrinsic extender 300. As there, regarding the first, distal, breakoff section 250, offsetting of the second breakoff 350 is especially beneficial after the cap 400 has been broken from the intrinsic extender 300, because the broken breakoff section 350 may have some roughness, for instance, that can be better avoided with the section 350 being setback from adjacent material in this way.

The offsetting also makes the portion gentler on any adjacent patient tissue after the break, as compared to the broken section 350 extending further or fully to proximal side surfaces of the intrinsic extender 300.

An outer diameter (OD) of the guide cap 400 may be greater than an OD of the intrinsic extender 300, as indicated by distance 452 in FIG. 3. Benefits of the larger relative OD include easier handling, including grasping, of the guide cap 400, manually or by tool, instrument, or machine. Benefits can also include snapping of the guide cap 400 from the extender 300 at the proximal breakoff 450 being easier.

FIGS. 3 and 4 show cutouts 456 of the guide cap 400, which may be curved or arched illustrated. Use herein of the term cutout does not limit the manner in which the associated geometry is formed. The related surfacing 456 does not have to be formed by cutting, or even machining, but can be. The cutouts 456 may be referenced herein, including in the claims, by other terms, such as transition portions 456.

In various embodiments, each cutout 456 has a surface 455 extending at an angle with respect to an adjacent side wall of the cap 400 and/or a side wall of the extender of between about 30 and 60 degrees, such as between about 40 and 50 degrees, such as approximately 45 degrees, all as shown in FIG. 4.

The cutouts 456 provide various benefits, including lowering weight, material for making, and cost, increasing in-procedure visibility, improved handling by a surgeon or assistance. The side low-profile transition portions 356 can also be viewed to create cutout sections instead of or along with the guide cap cutouts 456, to provide the same or similar benefits just mentioned in connection with, e.g., opposing, the cap cutouts 456, or increase the same benefits (even greater handleability, e.g.) when used with cap cutouts 456. The cutouts 456, the distal transition portions 356, or the two together can also provide robust clearance helpful in snapping the cap 400 from the extender 300 by moment along either direction 351 called out in FIG. 4.

Figure 7:
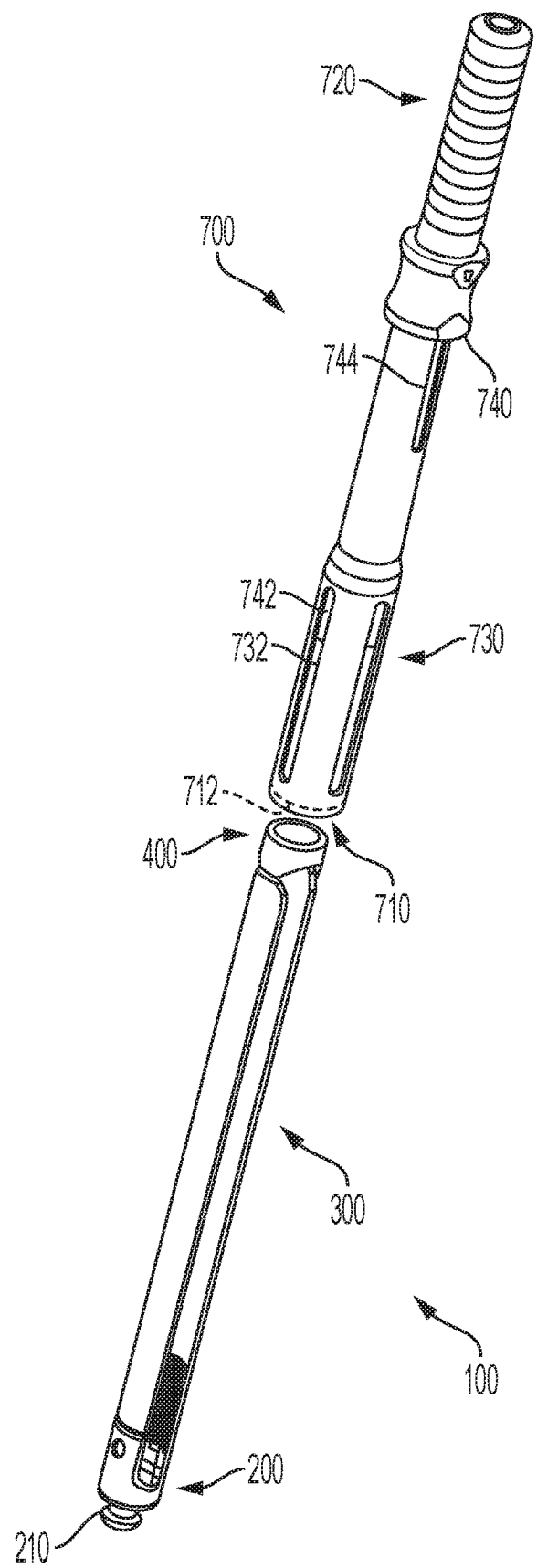
FIG. 7 shows a guide-cap remover instrument adjacent the monolithic percutaneous pedicle screw system.

A central or longitudinal axis is referenced by numeral 10 in FIGS. 3 and 4. Though not shown in every view, the axis represents the longitudinal axis for the system 100 as a whole, the components thereof 200, 300, 400, and for extrinsic parts and tools, such as the set screw 1350 (FIG. 13), instruments guided through the system channel, such as setscrew driver (not shown) or bone-filler device (not shown), and the multiple-cap removing-and-holding instrument 700 (FIG. 7).

The guide cap 400 include a proximal radially inner transition portion 420, in various embodiments. The transition portion 420 can be a curved or beveled surface. The proximal internal transition portion can provide analogous benefits to any of the benefits described above regarding other transition portions. The proximal internal transition portion 420 can also facilitate positioning (e.g., easier or otherwise better guiding) of media, such as instruments (e.g., a setscrew-driver or bone-filler tool), such as a setscrew driver (not shown), into and in the channel 430 formed by the cap 400 as well as into and in the aligned proximal channeling defined by the extender 300 and receiver 220.

The guide cap 400 also includes a retention feature 460 adjacent its proximal end in various embodiments. The retention features 460 can include an inward protrusion or lip 462.

The retention feature 460 can be configured to engage a corresponding retention feature (not shown) of a driver, bone filler, or other instrument placed into the cap 400, by the instrument catching or attaching to the retention feature 460 of the cap for provisional retention of the retention feature of the instrument, and so of the instrument, in a desired position there with respect to the cap 400. The instrument retention feature has a geometry corresponding to geometry (e.g., size and shape) of the retention featured 460. The instrument may have a groove or other shaping machined or otherwise formed into an outer surface of the instrument, such as a distal or proximal surface, of the instrument, corresponding to the geometry of the cap retention features 460, for example.

Figure 6:
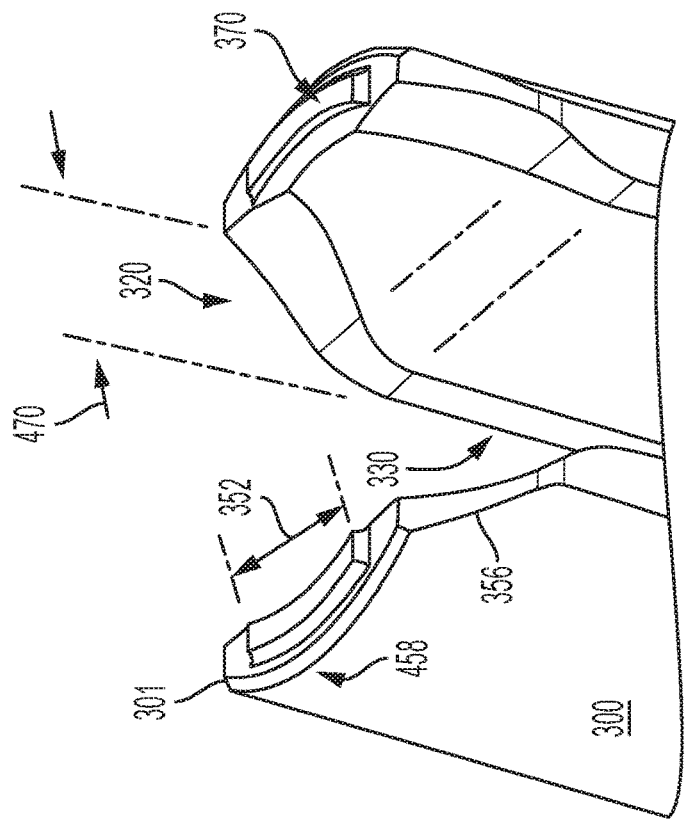
FIG. 6 is a perspective view of the proximal portion of the intrinsic extender after the guide cap has been broken off of the extender.
Figure 5:
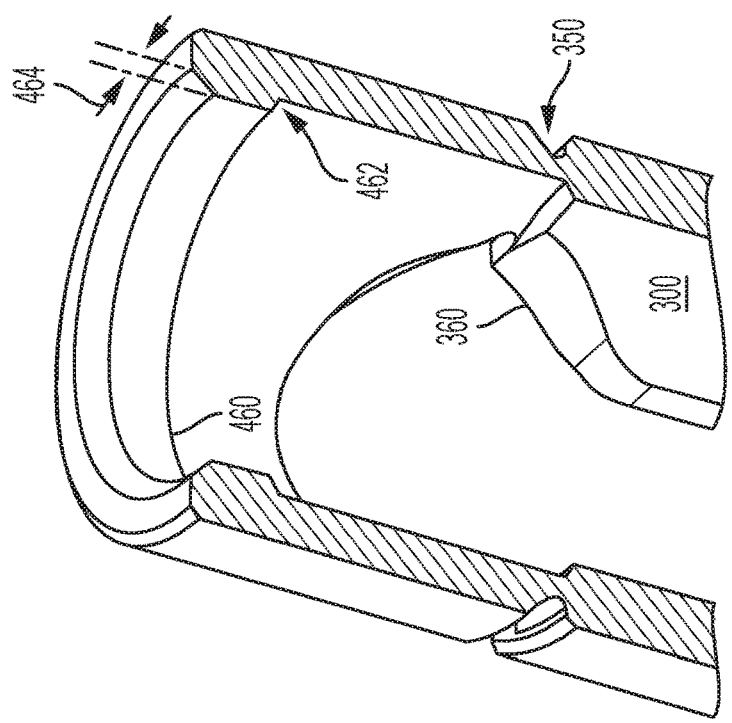
FIG. 5 is a perspective cross-section of the parts in FIG. 3.

FIG. 6 is a perspective view of the proximal portion of the intrinsic extender 300 after the guide cap has been broken off of the extender 300 at the proximal breakoff section 350. A section 370 of the breakoff section 350 remains at the proximal end of the intrinsic extender 300.

As also shown in FIG. 6, the intrinsic extender 300 can include a transition surface 320 extending between a proximal end 301 of the extender 300 an intermediate inner wall 320 of the extender 300. The transition surface 320 can have various benefits, including by providing a higher relative strength distal of the surface 320, where a wall of the extender 300 (is thickest, or at least thicker than the extender wall is at the proximal-surface), while lowering lower material cost and weight. The transition surface 320 can also promote implant and instrument guidance, such as by guiding the setscrew 1350 (FIG. 1350), a setscrew driver (not shown), or bone-filler device (not shown), to stay along the central axis 10 (shown in FIGS. 4 and 5) from the channel of the cap 400 down through the channel of the extender 300 to the rod slot of the receiver 220.

In various embodiments, the extenders 300, due to the transitions 320, transition from having a proximal separation between them, matching generally an inner diameter of the guide cap 400, to a distal separation between them matching generally an inner diameter defined by inside walls of the receiver arms 222.

FIG. 7 shows the multiple-cap removing-and-holding instrument 700 adjacent the monolithic percutaneous pedicle screw system 100. The instrument is in various embodiments configured to remove and hold multiple guide caps 400, and so be referred to as a multiple-cap remover, a multi-cap-remover tool or instrument, or the like.

By being able to hold multiple caps at a time, the multiple-cap removing-and-holding instrument 700 saves movement and time in surgery, by obviating the need to empty the receiver after each cap 400 is removed, or to use a separate remover for each cap.

The multiple-cap removing-and-holding instrument 700 extends from a distal cap-receiving end 710 to a proximal handle end 720. The proximal end 710 is configured (e.g., sized and shaped) to receive into an interior of the proximal end, a cap 400 of the system 100.

The multiple-cap removing-and-holding instrument 700 can further include a compartment 730 for holding one or more caps 400. The compartment 730 in various embodiments is a magazine, for holding multiple caps 400. The compartment 730 has side walls defining one or more windows or openings 732, in various embodiments, providing visibility to its interior, allowing a user to see whether and, if any, how many caps 400 are in the compartment 730.

The multiple-cap removing-and-holding instrument 700 can also include in the compartment 730 an internal cap-pushing device, such as a plunger 742 movable with respect to the side walls of the compartment 730. The remover is configured such that a user can manipulate the remover to push the plunger 742 distally to push down on one or more caps stored in the compartment 730, to eject the caps from the remover 700. This makes room for the guide-cap remover 700 to be used subsequently for capture more caps 400.

The guide-cap remover 700 can include cap-retaining structure 712 adjacent its proximal end 710. The cap-retaining structure 712 is configured (e.g., geometry (size, shape)) so that the proximal end 710 of the remover 700 can be slide over a guide cap 400 readily, with relative ease. The cap-retaining structure 712 is further configured such that a guide cap 400 captured by the remover 700, upon passing the structure 712, cannot easily fall out of the proximal end 710, such as by simple effect of gravity, or moving the remover 700 about the operating room, etc. The cap-retaining structure 712 is still further configured such that any captured guide caps 400 can be pushed proximally past the structure 712 by a cap-expelling sub-system of the remover 700, such as one including the plunger 742. In embodiments, the cap-retaining component 712 includes a lip 712 containing material, such as a plastic or rubber, that is softer than material of the chamber wall, which may include metal, for instance. The softer material gives as caps are pushed into our out of the compartment, but keeps them in when the only force on the cap/s is gravity or per usual, non-cap-expelling activity, by the user, so as not to fall out prematurely. This flexibility can instead or also be provided by slots in the distal end, so that the end includes fingers that can bend radially outward when pushed by a cap 400. This feature is also considered indicated schematically the reference numeral 712.

Figure 8:
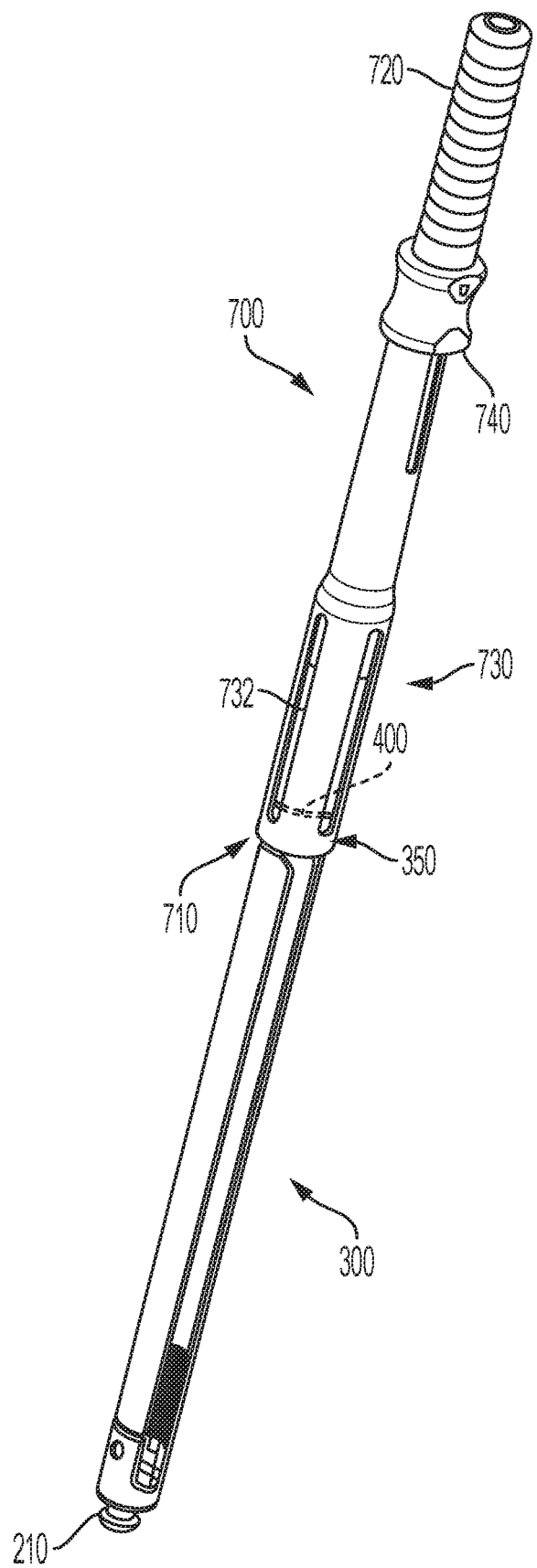
FIG. 8 shows the guide-cap remover instrument positioned over the guide cap of the system.

FIG. 8 shows the guide-cap remover instrument 700 having been positioned over the guide cap 700 of the system 100.

FIG. 9 is a closer view of the remover instrument 700 retrieving the guide cap 400.

Figure 10:
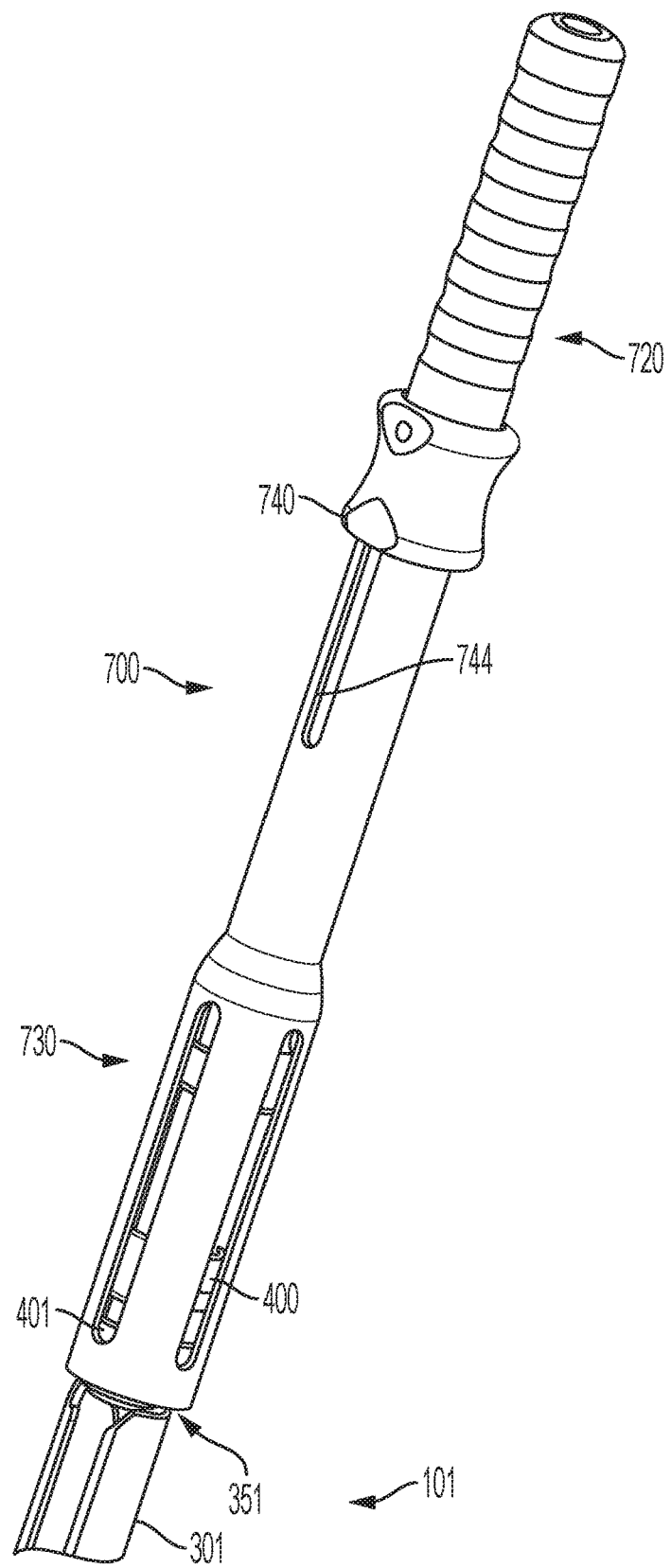
FIG. 10 shows the remover instrument holding the guide cap removed from the first monolithic percutaneous pedicle screw system, of FIG. 1, and positioned over a second guide cap of a second monolithic percutaneous pedicle screw system, like the system of FIG. 1, for forming a multi-system spinal construct in a patient.
Figure 11:
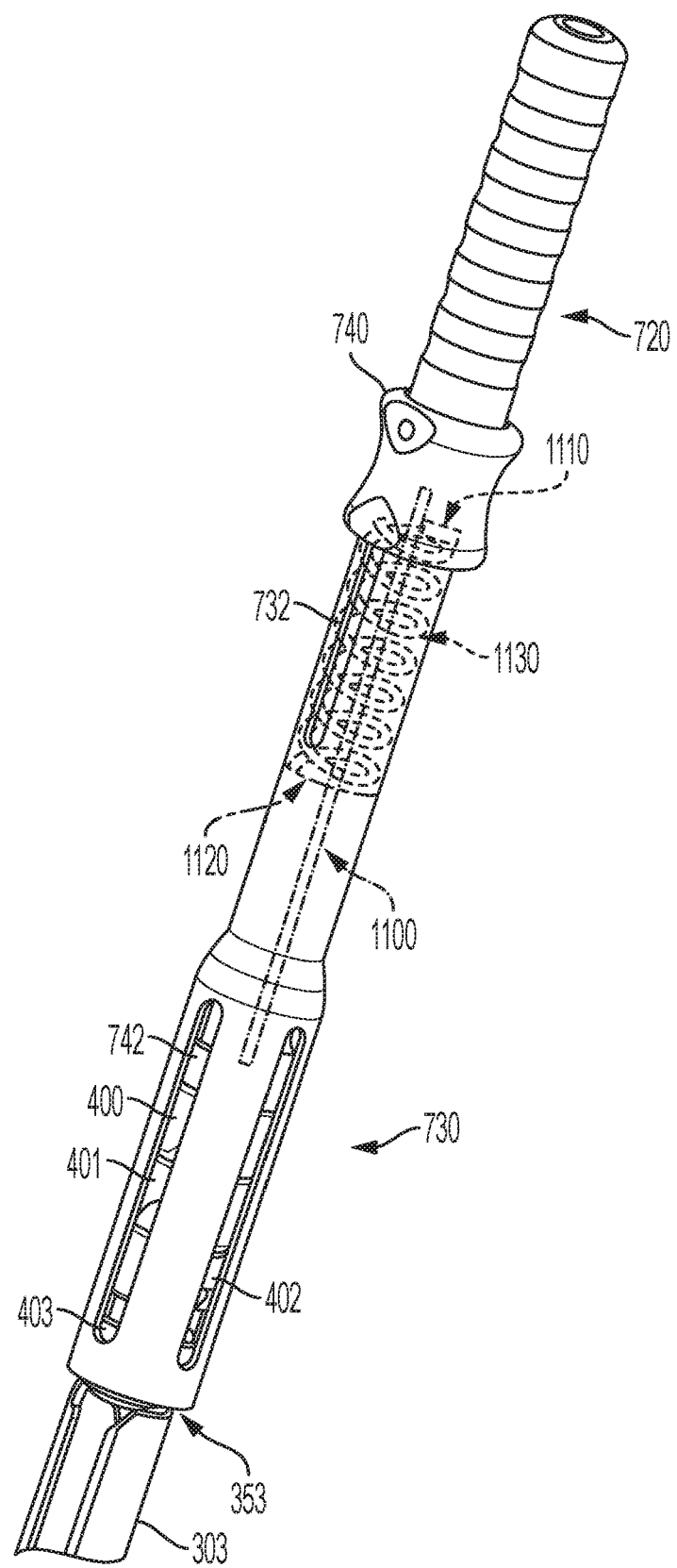
FIG. 11 shows the remover instrument holding first, second, and third guide caps removed from corresponding monolithic percutaneous pedicle screw systems, and positioned over a second guide cap of a fourth monolithic percutaneous pedicle screw system, like the system of FIG. 1, for forming a multi-system spinal construct in a patient.

FIG. 10 shows the remover instrument 700 holding the guide cap 400 removed from the first monolithic percutaneous pedicle screw system 100, of FIG. 1, and positioned over a second guide cap 401 of a second monolithic percutaneous pedicle screw system 101, like the system of FIG. 1, for forming a multi-system spinal construct in a patient;

FIG. 11 shows the remover instrument 700 holding first, second, and third guide caps 400, 401, 402 removed from corresponding monolithic percutaneous pedicle screw systems, and positioned over a fourth guide cap 403 of a second monolithic percutaneous pedicle screw system, like the system of FIG. 1, for forming a multi-system spinal construct in a patient (not shown).

Figure 12:
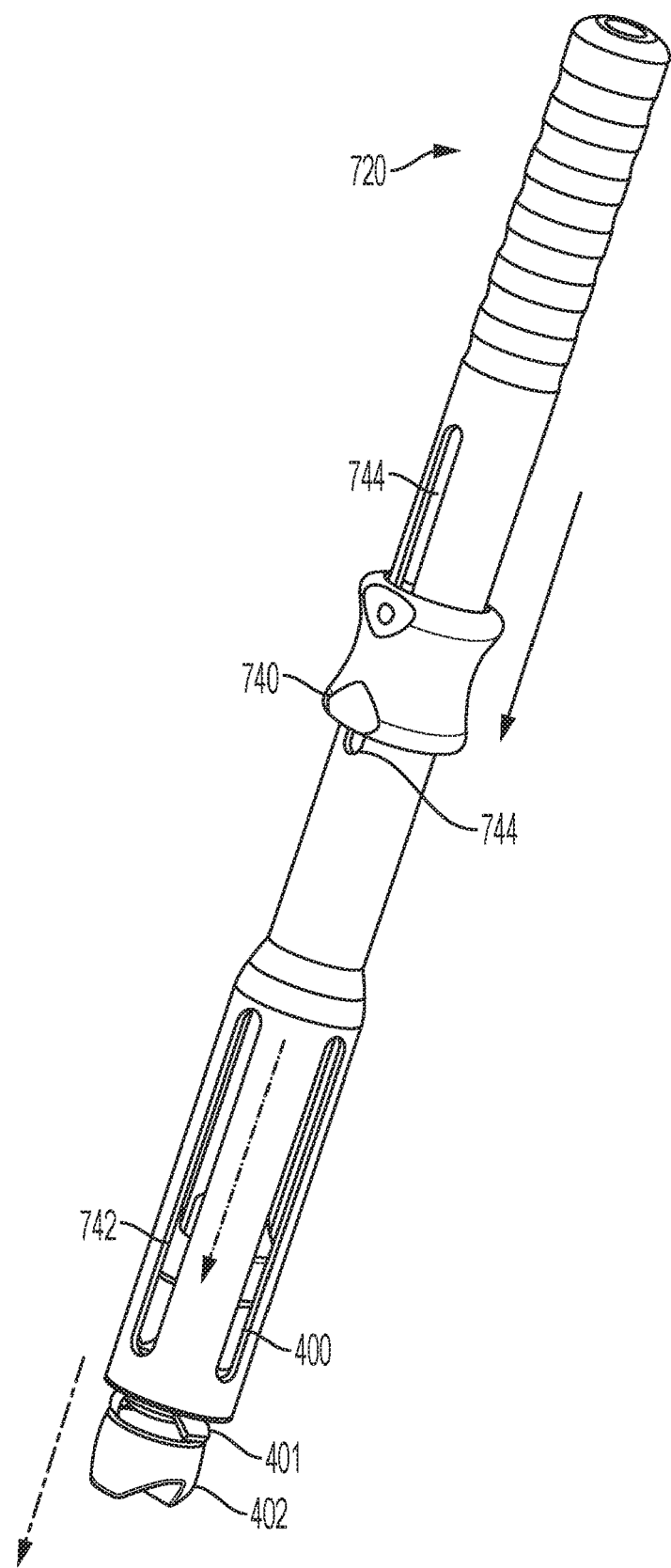
FIG. 12 shows dispelling of guide caps from the cap remover instrument by action of a plunger sub-system of the instrument.

FIG. 12 shows dispelling of guide caps from the cap remover instrument by action of the cap-pushing device of the instrument 700, such as a device including the plunger 742.

In various embodiments, as shown in FIG. 11, the multiple-cap removing-and-holding instrument 700 has a spring foundation 1120, such as a flange, on which a spring 1130 sits or to which the spring is connected.

The spring 1130 is positioned within the body—intermediate the handle 720 and the compartment 730, e.g.—and in contact with the sliding component 740 to bias the sliding component proximally. The sliding component 740 in some cases includes a collar 740 extending around the body. The instrument 700 has an elongated actuator 1100 connecting the sliding component 740 to the plunger 742. In some cases, the spring at least partially surrounds the elongated actuator 1100 within the body.

In various embodiments, the body portion has a body wall defining a longitudinal slot 744 (FIG. 10). The sliding component 740 may have or be connected to a collar-actuator component 1110 connecting the sliding component 740 to the elongated actuator 1100, the collar-actuator component 1110 being slidably disposed in the slot 744.

Thus, the collar 740 is connected by the elongated actuator 1100 to the plunger 742, such that when the collar 740 is pushed distally by a user, the collar, connected to the actuator 1100, causes the elongated actuator 1100 to push the plunger 742 down, distally within the compartment 730. The plunger 742 is thus pushed down against any guide caps 400 positioned in the compartment 730, until the cap/s 400 are pushed out of the distal end of the instrument 700, beyond any distal cap-retaining structure 712, thereby being ejected or expelled from the instrument 700.

Figure 13:
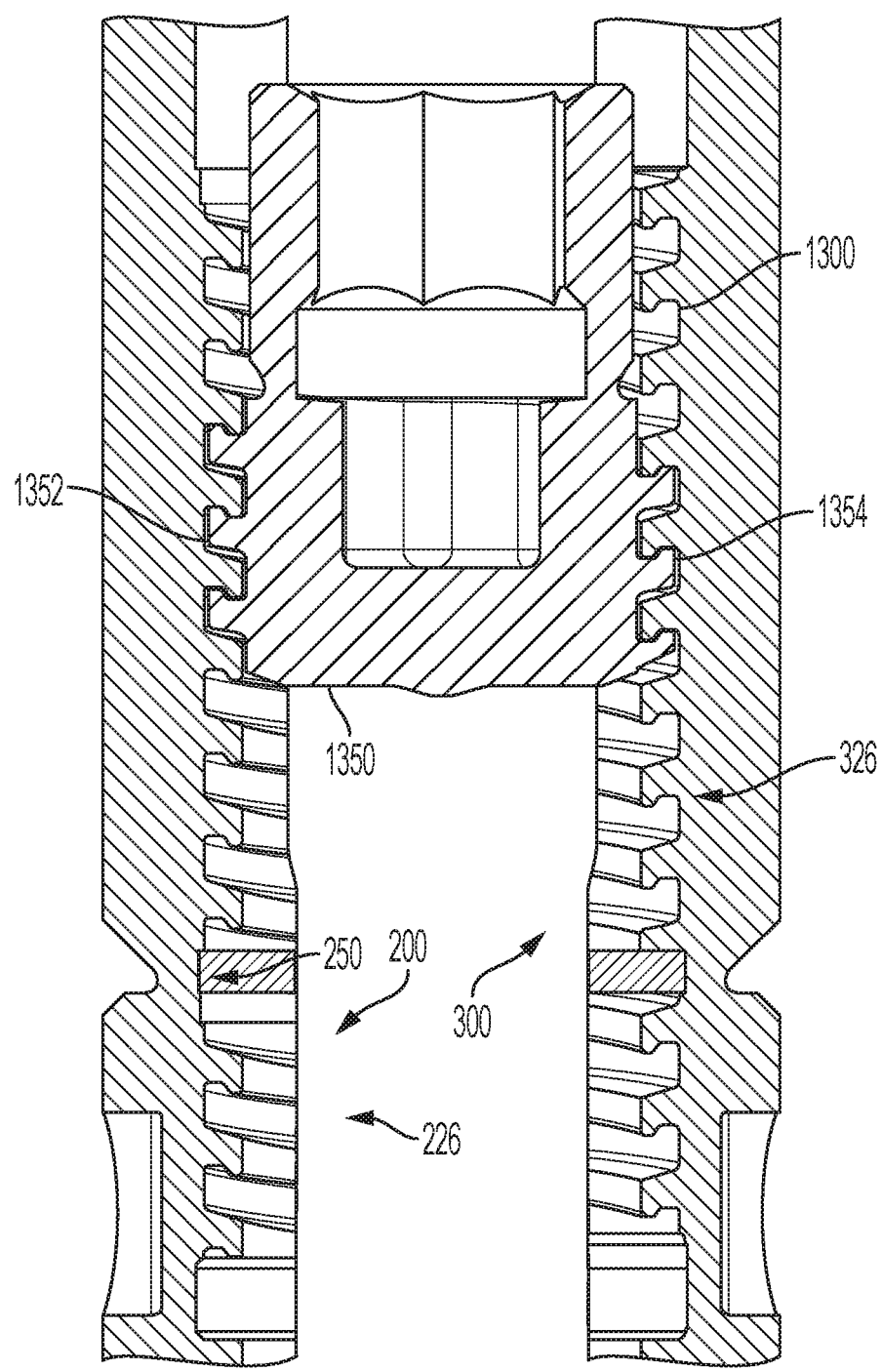
FIG. 13 is a side cross-section of a proximal portion of a receiver assembly and a distal portion of an intrinsic extender both having a helical-flange threadform for receiving a helical-flanged setscrew.

FIG. 13 is a side cross-section of a proximal portion of the receiver assembly 200 and a distal portion of the intrinsic extender 300 both having a helical-flange threadform for receiving a helical-flanged setscrew 1350, according to various embodiments of the present technology. The threadforms 226, 326 in these embodiments include a proximal flange-receiving space 1300 for receiving a proximal flange 1354 of each thread section 1352. Benefits of the flanged threadform include reducing splay, or moving apart of the arms 222, of the receiver 220. This can be especially helpful when the receiver 220 or at least the arms 222 have a material that has more of a tendency to splay, but has other benefits, such as weight, cost, or machinability.

It should be understood that various aspects disclosed herein may be combined in combinations other than the combinations presented specifically in the description and the accompanying drawings. It should also be understood that, depending on the example, certain acts or events of any of the processes or methods described herein may be performed in other sequence, added, merged, or left out altogether (e.g., all described acts or events may not be necessary to carry out the techniques).

In addition, while certain aspects of this disclosure are described as being performed by a single module or unit for purposes of clarity, it should be understood that the techniques of this disclosure may be performed by a combination of units or modules associated with, for example, a medical device.

Unless defined specifically otherwise herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an," and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed:

1. A monolithic percutaneous-screw system for use in spinal surgery, the system comprising:
   a receiver having a distal base and a pair of opposing arms extending proximally from the base;
   a pair of opposing distal breakoff sections, each connected monolithically to a proximal end of a corresponding one of the arms;
   a pair of opposing proximal breakoff sections;
   a pair of opposing intermediate extenders each comprising an outer wall and an inner wall, the outer walls each extending from a distal end, connected monolithically to a corresponding one of the pair of opposing distal breakoff sections, to a proximal end connected monolithically to a corresponding one of the pair of opposing proximal breakoff sections; and
   a guide cap connected monolithically to both of the proximal breakoff sections, the guide cap defining a proximal opening having a circular cross-sectional configuration and a passageway in communication with the opening, the inner walls being joined proximal to the opposing proximal breakoff sections to define a body that is positioned within the passageway;
   wherein:
   the pair of opposing proximal breakoff sections are each recessed inwardly from an outer surface of one of the pair of intermediate extenders and an outer surface of the guide cap;
   the pair of opposing proximal breakoff sections are each sized and shaped such that the pair of opposing proximal breakoff sections can be readily broken by a user when a first moment, along a first plane, is applied to the guide cap; and
   the pair of opposing distal breakoff sections are each sized and shaped such that each of the pair of opposing distal breakoff sections (i) is not broken when a user applies the first moment to the guide cap, and (ii) can be readily broken by the user when a second moment, along a second plane, generally orthogonal to the first plane, is applied to the pair of opposing intermediate extenders.

2. A monolithic percutaneous-screw system for use in spinal surgery, the system comprising:
   a receiver having a distal base and a pair of opposing arms extending proximally from the base;
   a pair of opposing distal breakoff sections, each connected monolithically to a proximal end of a corresponding one of the pair of opposing arms;
   a pair of opposing proximal breakoff sections;
   a pair of opposing intermediate extenders each comprising an outer wall and an inner wall, the outer walls each extending from a distal end, connected monolithically to a corresponding one of the pair of opposing distal breakoff sections, to a proximal end connected monolithically to a corresponding one of the pair of opposing proximal breakoff sections; and
   a guide cap connected monolithically to both of the pair of opposing proximal breakoff sections, the guide cap defining a proximal opening having a circular cross-sectional configuration and a passageway in communication with the opening, the inner walls converging proximal to the opposing proximal breakoff sections to define a body that is positioned within the passageway;
   wherein:
   the pair of opposing proximal breakoff sections are each recessed inwardly from an outer surface of one of the pair of intermediate extenders and an outer surface of the guide cap;
   an outer lateral surface of each of the pair of opposing distal breakoff sections is setback from an adjacent outer surface of a corresponding one of the pair of opposing arms connected to the pair of opposing distal breakoff sections;
   each of two end surfaces of each of the pair of opposing distal breakoff sections is setback from an adjacent side surface of a corresponding one of the pair of opposing arms connected to the pair of opposing distal breakoff sections;
   an outer lateral surface of each of the pair of opposing proximal breakoff sections is setback from an adjacent outer surface of a corresponding one of the pair of opposing intermediate extenders connected to the pair of opposing proximal breakoff sections; and
   each of two end surfaces of each of the pair of opposing proximal breakoff sections is setback from an adjacent side surface of a corresponding one of the pair of opposing intermediate extenders connected to the pair of opposing proximal breakoff sections.

3. A monolithic percutaneous-screw system for use in spinal surgery, the system comprising:
- a receiver having a distal base and a pair of opposing arms extending proximally from the distal base;
- a pair of opposing distal breakoff sections, each connected monolithically to a proximal end of a corresponding one of the pair of opposing arms;
- a pair of opposing proximal breakoff sections;
- a pair of opposing intermediate extenders each comprising an outer wall and an inner wall, the outer walls each extending from a distal end, connected monolithically to a corresponding one of the pair of opposing distal breakoff sections, to a proximal end connected monolithically to a corresponding one of the pair of opposing proximal breakoff sections; and
- a guide cap connected monolithically to both of the pair of opposing proximal breakoff sections, the guide cap defining a proximal opening having a circular cross-sectional configuration and a passageway in communication with the opening, the inner walls converging proximal to the opposing proximal breakoff sections to define a body that is positioned within the passageway,
- wherein the pair of opposing proximal breakoff sections are each recessed inwardly from an outer surface of one of the pair of intermediate extenders and an outer surface of the guide cap.

4. The monolithic percutaneous-screw system of claim 3, wherein:
- the pair of opposing proximal breakoff sections are each sized and shaped such that each of the pair of opposing proximal breakoff sections can be readily broken by a user when a first moment, along a first plane, is applied to the guide cap;
- the pair of opposing distal breakoff sections are each sized and shaped such that each of the pair of opposing distal breakoff sections (i) is not broken when a user applies the first moment to the guide cap, and (ii) can be readily broken by the user when a second moment, along a second plane, generally orthogonal to the first plane, is applied to the pair of opposing intermediate extenders; and
- a size of the pair of opposing proximal breakoff sections includes the pair of opposing proximal breakoff sections having a short length, measured between ends of the proximal breakoff section, as compared to a length of the pair of opposing distal breakoff sections, measured between ends of the pair of opposing distal breakoff sections.

5. The monolithic percutaneous-screw system of claim 3,
- the pair of opposing proximal breakoff sections are each sized and shaped such that each of the pair of opposing proximal breakoff sections can be readily broken by a user when a first moment, along a first plane, is applied to the guide cap;
- the pair of opposing distal breakoff sections are each sized and shaped such that each of the pair of opposing distal breakoff sections (i) is not broken when a user applies the first moment to the guide cap, and (ii) can be readily broken by the user when a second moment, along a second plane, generally orthogonal to the first plane, is applied to the pair of opposing intermediate extenders; and
- a shape of the pair of opposing distal breakoff sections includes lateral surfaces of the pair of opposing distal breakoff sections being concave.

6. The monolithic percutaneous-screw system of claim 3, wherein an outer lateral surface of each of the pair of opposing distal breakoff sections is setback from an adjacent outer surface of a corresponding one of the pair of opposing arms connected to the pair of opposing distal breakoff sections.

7. The monolithic percutaneous-screw system of claim 3, wherein an outer lateral surface of each of the pair of opposing distal breakoff sections is setback from an adjacent outer surface of a corresponding one of the pair of opposing intermediate extenders connected to the pair of opposing distal breakoff sections.

8. The monolithic percutaneous-screw system of claim 3, each of two end surfaces of each of the pair of opposing distal breakoff sections is setback from an adjacent side surface of a corresponding one of the pair of opposing arms connected to the pair of opposing distal breakoff sections.

9. The monolithic percutaneous-screw system of claim 3, each of two end surfaces of each of the pair of opposing distal breakoff sections is setback from an adjacent side surface of a corresponding one of the pair of opposing intermediate extenders connected to the pair of opposing distal breakoff sections.

10. The monolithic percutaneous-screw system of claim 3, wherein an outer lateral surface of each of the pair of opposing proximal breakoff sections is setback from an adjacent outer surface of the outer wall of a corresponding one of the pair of opposing intermediate extenders.

11. The monolithic percutaneous-screw system of claim 3, wherein an outer lateral surface of each of the pair of opposing proximal breakoff sections is setback from an adjacent outer surface of the guide cap connected to the pair of opposing proximal breakoff sections.

12. The monolithic percutaneous-screw system of claim 3, wherein each of two end surfaces of each of the pair of opposing proximal breakoff sections is setback from an adjacent side surface of the outer wall of a corresponding one of the pair of opposing intermediate extenders.

13. The monolithic percutaneous-screw system of claim 3, wherein each of two end surfaces of each of the pair of opposing proximal breakoff sections is setback from an adjacent outer surface of the guide cap connected to the pair of opposing proximal breakoff sections.

14. The monolithic percutaneous-screw system of claim 3, wherein:
- the inner walls each have an extender threadform;
- each of the pair of opposing arms has an inner wall and an outer wall, the inner walls of the arms each having a receiver threadform; and
- the extender threadforms are sized, shaped, and clocked to match the receiver threadform such that a setscrew can thread smoothly through the extender threadforms proximally onto the receiver threadform.

15. The monolithic percutaneous-screw system of claim 14, wherein
- each threadform has a helical flange format for receiving a helical-flange setscrew, the threadform defining a thread channel comprising a proximally extending space for receiving a proximally extending flange of a setscrew thread.

16. The monolithic percutaneous-screw system of claim 3, wherein the guide cap has a proximal end having a circular cross section, the proximal end of the guide cap defining the proximal opening.

17. The monolithic percutaneous-screw system of claim 16, wherein the proximal end of the guide cap comprises a radially inner transition portion having a curved or beveled surface to facilitate guiding external media into a central channel of the guide cap in operation of the system.

18. The monolithic percutaneous-screw system of claim 16, wherein the guide cap has opposing arched distal cutouts.

19. The monolithic percutaneous-screw system of claim 16, wherein:
- the guide cap has opposing arched distal cutouts; and
- each of the interface comprises opposing transition surfaces sloping from proximal ends of the pair of intermediate extenders to a corresponding side wall of the pair of intermediate extenders, each sloping surface opposing one of the opposing arched distal cutouts.

20. The monolithic percutaneous-screw system of claim 19, wherein:
- each of the opposing transition surfaces extends with respect to an adjacent side wall of the pair of intermediate extenders by an angle of between about 30 degrees and about 60 degrees; and
- each of the opposing distal cutouts extends with respect to an adjacent exterior wall of the guide cap by an angle of between about 30 degrees and about 60 degrees.

* * * * *